US008754213B2

(12) United States Patent
Hoorne-van Gemert et al.

(10) Patent No.: US 8,754,213 B2
(45) Date of Patent: Jun. 17, 2014

(54) HIGH FLOW SUPRAMOLECULAR COMPOUNDS

(75) Inventors: Gaby Maria Leonarda Hoorne-van Gemert, Landgraaf (NL); Sandrine Chodorowski-Kimmès, Senlis (FR); Henricus Marie Janssen, Eindhoven (NL); Egbert Willem Meijer, Waalre (NL); Anton Willem Bosman, Eindhoven (NL)

(73) Assignee: SupraPolix B.V., Eindhoven (NL)

( * ) Notice: Subject to any disclaimer, the term of this patent is extended or adjusted under 35 U.S.C. 154(b) by 622 days.

(21) Appl. No.: 13/002,500

(22) PCT Filed: Jul. 6, 2009

(86) PCT No.: PCT/NL2009/050401
§ 371 (c)(1),
(2), (4) Date: May 19, 2011

(87) PCT Pub. No.: WO2010/002262
PCT Pub. Date: Jan. 7, 2010

(65) Prior Publication Data
US 2011/0229724 A1    Sep. 22, 2011

Related U.S. Application Data

(60) Provisional application No. 61/078,459, filed on Jul. 7, 2008.

(30) Foreign Application Priority Data

Jul. 4, 2008 (EP) ..................................... 08159764

(51) Int. Cl.
C07D 239/02 (2006.01)
C07D 239/47 (2006.01)
C07D 239/48 (2006.01)

(52) U.S. Cl.
CPC ............ *C07D 239/47* (2013.01); *C07D 239/48* (2013.01)
USPC .......................................... 544/320; 544/328

(58) Field of Classification Search
CPC ........................... C07D 239/47; C07D 239/48
USPC .................................................. 544/320, 321
See application file for complete search history.

(56) References Cited

U.S. PATENT DOCUMENTS

| | | | |
|---|---|---|---|
| 3,375,800 A | 4/1968 | Cole et al. | |
| 3,388,087 A | 6/1968 | Dieterich et al. | |
| 3,480,592 A | 11/1969 | Dieterich et al. | |
| 4,093,759 A | 6/1978 | Otsuki et al. | |
| 4,136,092 A | 1/1979 | Jackle et al. | |
| 4,140,759 A | 2/1979 | Mausner | |
| 4,216,318 A | 8/1980 | Brown et al. | |
| 4,229,838 A | 10/1980 | Mano | |
| 4,322,327 A | 3/1982 | Yoshimura et al. | |
| 4,684,728 A | 8/1987 | Mohring et al. | |
| 4,942,035 A | 7/1990 | Churchill et al. | |
| 5,410,016 A | 4/1995 | Hubbell et al. | |
| 5,500,209 A | 3/1996 | Ross et al. | |
| 5,548,035 A | 8/1996 | Kim et al. | |
| 5,610,268 A | 3/1997 | Meijer et al. | |
| 5,631,337 A | 5/1997 | Sassi et al. | |
| 5,723,563 A | 3/1998 | Lawrey et al. | |
| 5,736,535 A | 4/1998 | Bernstein et al. | |
| 5,874,069 A | 2/1999 | Mendolia et al. | |
| 5,883,211 A | 3/1999 | Sassi et al. | |
| 5,919,441 A | 7/1999 | Mendolia et al. | |
| 6,320,018 B1 * | 11/2001 | Sijbesma et al. | 528/310 |
| 6,353,076 B1 | 3/2002 | Barr et al. | |
| 6,489,397 B2 | 12/2002 | Kim et al. | |
| 6,534,072 B2 | 3/2003 | Mondet et al. | |
| 6,683,135 B2 * | 1/2004 | Cruse et al. | 525/100 |
| 6,683,151 B1 | 1/2004 | Loontjens et al. | |
| 6,702,850 B1 | 3/2004 | Byun et al. | |
| 6,716,370 B2 | 4/2004 | Kendig | |
| 6,743,767 B2 | 6/2004 | Goldoni et al. | |
| 6,803,447 B2 * | 10/2004 | Janssen et al. | 528/423 |
| 6,803,477 B2 | 10/2004 | Prakash et al. | |
| 6,818,018 B1 | 11/2004 | Sawhney | |

(Continued)

FOREIGN PATENT DOCUMENTS

EP   0 259 92 A2   9/1983
EP   0 259 92 B1   9/1983

(Continued)

OTHER PUBLICATIONS

International Preliminary Report on Patentability, PCT/NL2009/050401 (Jan. 5, 2011).*
T. Park et al., Journal of the American Chemical Society, 14236-14237 (2006).*
V. Marin, Dalton Transactions, 1636-1644 (2006).*
Holger Schönherr, Polymer Preprints 1-2 (2003).*
S. Zou et al., 19 Langmuir, 8618-8621 (2003).*
Brunsveld, L et al., "Supramolecular Polymers", Chemical Reviews, vol. 101, 2001, pp. 4071-4097, XP002267453.

(Continued)

*Primary Examiner* — Deepak Rao
*Assistant Examiner* — Alexander R Pagano
(74) *Attorney, Agent, or Firm* — Gilberto M. Villacorta; Sunit Talapatra; Foley & Lardner LLP

(57) ABSTRACT

The present invention relates to a supramolecular compound comprising a low molecular weight, apolar compound, said low molecular weight, apolar compound having a melting point of below 45° C., a molecular weight of about 80 to about 1500 amu and a HLB-value of lower than 8, said low molecular weight, apolar compound bearing a single 4H-unit per molecule. The supramolecular compound according to the present invention may be used in coating, ink, toner, resin, lacquer, adhesive or glue compositions.

11 Claims, No Drawings

(56) References Cited

U.S. PATENT DOCUMENTS

| | | | |
|---|---|---|---|
| 6,899,992 B2 | 5/2005 | Huang et al. | |
| 6,911,296 B2 | 6/2005 | Pappas et al. | |
| 6,939,938 B2 | 9/2005 | Benard et al. | |
| 6,972,304 B2 | 12/2005 | Smith et al. | |
| 7,196,073 B2 | 3/2007 | Marciani | |
| 7,622,131 B2 * | 11/2009 | Bosman et al. | 424/401 |
| 7,683,104 B2 * | 3/2010 | Watanabe | 522/168 |
| 7,736,663 B2 | 6/2010 | Cooper et al. | |
| 7,838,621 B2 * | 11/2010 | Janssen et al. | 528/327 |
| 7,862,805 B2 | 1/2011 | Mougin et al. | |
| 8,247,524 B2 * | 8/2012 | Janssen et al. | 528/327 |
| 2003/0015185 A1 | 1/2003 | Dutart | |
| 2003/0092838 A1 | 5/2003 | Fomperie et al. | |
| 2003/0158403 A1 | 8/2003 | Manoharan et al. | |
| 2004/0023155 A1 | 2/2004 | Hayakawa et al. | |
| 2004/0034190 A1 * | 2/2004 | Janssen et al. | 528/423 |
| 2004/0087755 A1 | 5/2004 | Eling et al. | |
| 2007/0093639 A1 * | 4/2007 | Jassen et al. | 528/327 |
| 2007/0149751 A1 | 6/2007 | Lindsay et al. | |
| 2007/0264208 A1 | 11/2007 | Mougin et al. | |
| 2008/0260795 A1 * | 10/2008 | Baughman et al. | 424/423 |
| 2009/0004274 A1 | 1/2009 | Hoorne-Van Gemert et al. | |
| 2009/0111930 A1 * | 4/2009 | van Gemert et al. | 524/498 |
| 2009/0130172 A1 | 5/2009 | Dankers et al. | |
| 2010/0028277 A1 * | 2/2010 | Chodorowski-Kimmes et al. | 424/59 |
| 2010/0076147 A1 * | 3/2010 | Hoorne-Van Gemert et al. | 524/548 |
| 2011/0034641 A1 * | 2/2011 | Janssen et al. | 525/454 |
| 2012/0116014 A1 * | 5/2012 | Janssen et al. | 524/590 |
| 2012/0136120 A1 * | 5/2012 | Bosman | 525/123 |

FOREIGN PATENT DOCUMENTS

| | | |
|---|---|---|
| EP | 0 433 188 A1 | 6/1991 |
| EP | 0 744 428 A2 | 11/1996 |
| EP | 0 683 769 B1 | 7/1998 |
| EP | 0 877 055 B1 | 11/1998 |
| EP | 1 213 309 A | 6/2002 |
| EP | 0 877 055 A | 9/2004 |
| EP | 1 687 378 A1 | 8/2006 |
| EP | 1 310 533 B2 | 1/2007 |
| EP | 1 392 222 B1 | 9/2007 |
| EP | 2 450 394 A1 | 5/2012 |
| FR | 2657082 A1 | 7/1991 |
| FR | 2825628 B1 | 12/2002 |
| JP | 48-029398 B | 9/1973 |
| JP | 51-022823 A | 2/1976 |
| JP | 52-074692 A | 6/1977 |
| JP | 2004-250623 A | 9/2004 |
| SU | 910718 A1 | 3/1982 |
| WO | WO-98/14504 A1 | 4/1998 |
| WO | WO-98/14505 A1 | 4/1998 |
| WO | WO-98/23307 | 6/1998 |
| WO | WO-99/07343 A1 | 2/1999 |
| WO | WO-01/44307 | 6/2001 |
| WO | WO-02/34312 A1 | 5/2002 |
| WO | WO-02/46260 A1 | 6/2002 |
| WO | WO-02/098377 A1 | 12/2002 |
| WO | WO-03/032929 A2 | 4/2003 |
| WO | 1 310 533 A2 | 5/2003 |
| WO | WO-03/059964 A2 | 7/2003 |
| WO | WO-03/099875 A2 | 12/2003 |
| WO | WO 2004/016598 A1 | 2/2004 |
| WO | WO 2004016598 A1 * | 2/2004 |
| WO | WO-2004/052963 A1 | 6/2004 |
| WO | WO-2005/042641 A1 | 5/2005 |
| WO | WO-2006/006855 A1 | 1/2006 |
| WO | WO-2006/118460 A1 | 11/2006 |
| WO | WO-2006/118461 A2 | 11/2006 |
| WO | WO-2007/058539 A2 | 5/2007 |
| WO | WO 2007/072000 A1 | 6/2007 |
| WO | WO 2007072000 A1 * | 6/2007 |
| WO | WO 2008/063057 A2 | 5/2008 |
| WO | WO 2008063057 A2 * | 5/2008 |
| WO | WO-2010/002261 A1 | 1/2010 |
| WO | WO-2010/002262 A1 | 1/2010 |

OTHER PUBLICATIONS

Chemical Abstract, vol. 85, Abst. No. 15348y, Jul. 1976, 1 Page.
Chemical Abstracts, Vo. 97, No. 10, Sep. 1982, Veselovskii et al., "Adhesive Composition," Inst. of the Chemistry of High Molecular Weight Compounds, Mar. 5, 1979, 1 Page.
Chemical Abstracts, vol. 80, No. 20, May 20, 1974, English abstract of JP 04 829398, filed Aug. 28, 1968, 1 Page.
CRC Handbook of Chemistry & Physics, 59th Ed., p. E-61, 1978-1979, CRC Press, Inc, 3 Pages.
Derwent 91-179975125, 1 Page.
Derwent Abstract Acc. No. 1977-55084Y, Week 197731, English abstract for JP 52-74692, Jun. 22, 1977, 3 Pages.
Dieterich et al, "Polyurethane Inomers, a New Class of Block Polymers," Angew. Chem. Int'l. Edit., vol. 9, No. 1, 1970, p. 40-50 (English version of German article in Angew. Chem., vol. 2, 1970, pp. 53-63).
El-Ghayoury et al., "Supramolecular Hydrogen-Bonded Oligo($p$-phenylene vinylene) Polymers," Angew. Chem. Intl. Ed., vol. 40, No. 19, 2001, pp. 3660-3663. XP002260390.
Flory, P.J., "Random Reorganization of Molecular Weight Distribution in Linear Condensation Polymers," J. Am. Chem. Soc., 1942, vol. 64, pp. 2205-2212.
Folmer et al., "Supramolecular Polymer Materials: Chain Extension of Telechelic Polymers Using a Reactive Hydrogen-Bonding Synthon," Adv. Mater. 2000, vol. 12, No. 12, 874-878.
Guan et al., "Modular Domain Structure: A Biomimetic Strategy for Advanced Polymeric Materials," J. Am. Chem. Soc., vol. 126, 2004, pp. 2058-2065.
Guan et al., "Synthesis and Single-Molecule Studies of Modular Polymers Using Precise Hydrogen Bonding Interactions," Polymer Preprints, vol. 44(2), 2003, pp. 485-486.
Hirschberg et al., "Supramolecular Polymers from Linear Telechelic Siloxanes with Quadruple-Hydrogen-Bonded Units," Macromolecules, vol. 32, No. 8, 1999, pp. 2696-2705.
Hirschberg et al., "Ureidotriazine-Based Supramolecular Copoloymers" Marcomolecules, vol. 36, 2003, pp. 1429-1432.
Hofmeier et al., "New Supramolecular Polymers Containing Both Terpyridine Metal Complexes and Quadruple Hydrogen Bonding Units," Chem. Commun., 2004, pp. 318-319.
International Search Report mailed Oct. 24, 2005 for PCT/NL2005/000497, 3 Pages.
International Search Report, PCT/NL2006/050106, mailed Aug. 29, 2006, 4 Pages.
International Search Report, PCT/NL2006/050107, mailed Jul. 12, 2007, 3 Pages.
Kato T., "Supramolecular Liquid Crystal Polymers, Formation of Molecular Self-Organized Structures and Their Functionalization," Kobunshi Ronbunshu, vol. 54(12), 1997, pp. 855-862. (Abstract on last page).
Kautz et al., "Cooperative End-to-End and Lateral Hydrogen-Bonding Motifs in Supramolecular Thermoplastic Elastomers," Macromolecules, vol. 39, 2006, pp. 4265-4267.
Korshak et al., "Experimental Methods of Bulk Polymerization," Comprehensive Polymer Science: The Synthesis, Characterization, Reactions & Application of Polymers, vol. 5, 1989, Pergamon Press, pp. 131-142.
Lange et al., "Hydrogen-Bonded Supramolecular Polymer Networks," Journal of Polymer Science: Part A: Polymer Chemistry, vol. 37, 1999, pp. 3657-3670.
Lange et al., "Supramolecular Polymer Interactions Based on the Alternating Copolymer of Styrene and Maleimide," Macromolecules, vol. 28, 1995, pp. 782-783.
Lee et al., "Hydrogels for Tissue Engineering" Chem. Rev., vol. 101, No. 7, 2001, pp. 1869-1879.
Rieth et al., "Polymerization of Ureidopyrimidinone-Functionalized Olefins by Using Late-Transition Metal Ziegler-Natta Catalysts: Synthesis of Thermoplastic Elastomeric Polyolefins," Angew. Chem. Intl. Ed., vol. 40, No. 11, 2001, pp. 2153-2156.

(56) References Cited

OTHER PUBLICATIONS

Roland et al., "Synthesis of Titin-Mimicking Polymers Having Modular Structures by Using Noncovalent Interactions", Polymer Preprints, vol. 44(1), 2003, pp. 726-727.

Saunders et al. (editors), "Polyurethanes—Chemistry and Technology High Polymers: Part 1. Chemistry," High Polymers, vol. XVI-Part 1, 1962, Interscience Publishers a Division of Wiley & Sons, pp. 68-73.

Sijbesma et al., "Reversible Polymers Formed from Self-Complementary Monomers Using Quadruple Hydrogen Bonding," Science, vol. 278, 1997, pp. 1601-1604.

Urbanski et al. "Potential Antimalarial Compounds.sup.1. IX.sup.2. Pyrimidine Derivatives of Urea and Guanidine", Journal of Medicinal Chemistry, vol. 10, 1967, pp. 521-525.

Yamauchi et al., Abstract of "Synthesis and Characterization of Novel Multiple-Hydrogen Bonded Macromolecules Via A Michael Reaction," Dept. of Chemistry, Virginia Polytechnic Institute and State University.

Yamauchi et al., "Thermoreversible Poly(alkyl acrylates) Consisting of Self-Complementary Multiple Hydrogen Bonding," Macromolecules, vol. 36, 2003, pp. 1083-1088.

Yamauchi, et al., "Thermoreversible Polyesters Consisting of Multiple Hydrogen Bonding (MHB)," Macromolecules, vol. 37, No. 10, 2004, pp. 3519-3522.

Even et al., "Synthesis and characterization of amphiphilic triblock polymers by copper mediated living radical polymerization", European Polymer Journal, vol. 39, 2003, pp. 633-639.

Folmer et al., "Supramolecular Polymer Materials: Chain Extension of Telechelic Polymers Using a Reactive Hydrogen-Bonding Synthon," Adv. Mater., vol. 12, No. 12, 2000, pp. 874-878.

Cate et al., "Hydrogen-Bonded Supramolecular Polymers with Tunable Material Properties," Polymer Preprints, 44(1):618-619 (2003).

Hirschberg et al., "Helical Supramolecular Aggregates Based on Ureidopyrimidinone Quadruple Hydrogen Bonding," Chemistry—A European Journal, 9:4222-4231 (2003).

Kiriy et al., "Atomic Force Microscopy Visualization of Single Star Copolymer Molecules," Polymeric Materials: Science & Engineering, 88:233-234 (2003).

Matsuda et al., "Terminally Alkylated Heparin. 1. Antithrombogenic Surface Modifier," Biomacromolecules, 2:1169-1177 (2001).

Maynard et al., "Inhibition of Cell Adhesion to Fibronectin by Oligopeptide-Substituted Polynorbornenes," Journal of American Chemical Society, 123:1275-1279 (2001).

Menger et al., "Self-Adhesion Among Phospholipd Vesicles," Journal of the American Chemical Society, 128:1414-1415 (2006).

Rowley et al., "Alginate Hydrogels as Synthetic Extracellular Matrix Materials," Biomaterials, 20:45-53 (1999).

Uhrich et al., "Polymeric Systems for Controlled Drug Release," Chemical Reviews, 99:3181-3198 (1999).

Vulic et al., "Heparin-Containing Block Copolymers," Journal of Materials Science: Materials Medicine, 4:353-365 (1993).

International Search Report mailed Aug. 10, 2009 in International Application No. PCT/NL2009/050401.

\* cited by examiner

HIGH FLOW SUPRAMOLECULAR COMPOUNDS

FIELD OF THE INVENTION

The present invention relates to supramolecular compounds comprising only one quadruple hydrogen bonding unit per molecule that are obtained from low molecular weight apolar molecules that have melting points below 45° C. The resulting supramolecular compounds form solids that can be used in coating, adhesive and ink compositions while their melt-viscosity remains low. These unique new characteristics result from the presence of additional physical interactions between the compounds that are based on multiple hydrogen bonding interactions (supramolecular interactions).

BACKGROUND OF THE INVENTION

This invention relates to supramolecular compounds comprising a single quadruple hydrogen bonding unit that are capable of forming at least four H-bridges with each other in a row leading to physical interactions between different supramolecular compounds. These physical interactions originate from multiple hydrogen bonding interactions (supramolecular interactions) between self-complementary units comprising at least four hydrogen bonds in a row. Units capable of forming at least four hydrogen bonds in a row, i.e. quadruple hydrogen bonding units, are in this patent application abbreviated as 4H-units. Sijbesma et al. (U.S. Pat. No. 6,320,018; Science 1997, 278, 1601; incorporated by reference herein) discloses 4H-units that are based on 2-ureido-4-pyrimidones. These 2-ureido-4-pyrimidones in their turn are derived from isocytosines.

Polymers modified with two or three 4H-units have been prepared (Folmer, B. J. B. et al., Adv. Mater. 2000, Vol. 12, 874; Hirschberg et al., Macromolecules 1999, Vol. 32, 2696; Lange, R. F. M. et al., J. Polym. Sci. Part A, 1999, 37, 3657-3670; all incorporated by reference herein). However, these polymers need at least two 4H-units per chain in order to get a significant higher molecular weight via self-assembly, that is critically needed to obtain polymeric compound properties. Moreover, it has been reported that the presence of monofunctional 4H-units in these compounds leads to a strong decrease in their compound properties (Folmer, B. J. B., PhD thesis TU Eindhoven, 2000, Chapter 4; incorporated by reference).

Polymers with a relative large number of 4H-units grafted on the main chain have been obtained by copolymerizing an olefin bearing a 4H-unit with a common olefin (Coates, G. W. et al., Angew. Chem. Int. Ed., 2001, Vol. 40, 2153; incorporated by reference), or by copolymerizing a diisocyanate functional 4H-unit with polyether or polyester diols (EP 1.687.378; incorporated by reference). In this way, reversible cross-links are introduced via hydrogen bonding resulting in polymeric compound properties for these self-assembling polymers. However, in all these cases relative large molecular weight polymers are obtained resulting in relative large melt viscosities. Hence, efficient melt-processing of such compounds is limited.

Dyes containing only one 4H-unit are disclosed in EP 1.310.533, incorporated by reference, the resulting dyes are used in ink-jet compositions because of their increased light fastness. Examples are disclosed that are constituted from a 4H-unit coupled to aromatic dyes via linker molecules such as diisocyanates. However, because these dyes consist of large aromatic systems, their melting point is significant higher than 45° C. and therefore the resulting molecules are crystalline powders in nature and they do not show polymeric compound properties like good film forming and ductile behaviour.

Phase-change inks are disclosed in US 2003/0105185, incorporated by reference. These inks contain an ink-vehicle that is a compound containing one to four 4H-units per molecule. Glycerine and sucrose-based polyols functionalized with two to four 4H-units are disclosed in Examples V-VIII of this patent application, resulting in polymeric molecules of high molecular weights and therefore high melt viscosities. Additionally, in Example XVII, molecules are disclosed consisting of a 4H-unit with linear $C_1$ to $C_{18}$ alkyl-chains directly coupled to it, resulting in crystalline organic compounds with sharp melting points. Consequently, the monofunctional compounds in this Example XVII behave like normal organic compounds and do not show polymeric compound properties like good film forming and ductile behaviour.

Liquid-crystalline molecules containing one 4H-unit have been prepared (Hirschberg et al., Chem. Eur. J. 2003, 4222; incorporated by reference). In order to induce liquid crystallinity in these compounds it was necessary to have a large mesogenic system (3,4,5 tri-alkoxy phenyl) on the 6-position of the isocytosine ring that constitutes the 4H-unit. Therefore, multiple synthetic steps are necessary to obtain a precursor of the 4H-unit that contains this large aromatic system including the synthesis of a custom-made β-keto-ester. Moreover, the compound properties and possible applications of these compounds are not disclosed.

Water dispersable compounds containing one 4H-unit have been prepared (Menger et al., J. Am. Chem. Soc. 2006, 1414; incorporated by reference). The compound contains a cholesterol moiety linked to a 4H-unit via an oligoethylene glycol linker. This hydrophilic linker is needed to suspend the molecule into water as demonstrated in this paper. Clearly, this hydrophilicity excludes the use of this compound in applications were atmospheric water is present as this will have a detrimental effect on the compounds properties.

Example 9 of WO 2004/016598, incorporated by reference, discloses a compound having one 4H unit, said compound containing a polar PEG-MA group which is linked to the 4H unit by a hexamethylene group.

WO 2007/072000, incorporated by reference, discloses compounds according to Formula (II) wherein polymeric groups having a molecular weight of 200-500.000 are linked to at least two 4H units.

WO 2008/063057, incorporated by reference, discloses supramolecular polymers comprising 1-50 4H units by reacting 4H units bearing at least one functional group with a prepolymer having preferably at least two complementary functional groups.

There is a need in the art for low molecular weight supramolecular compounds having a low melt viscosity and which are easy to process and still show supramolecular behaviour. Such supramolecular compounds would be very useful for coating, adhesive and ink compositions.

SUMMARY OF THE INVENTION

The invention relates to supramolecular compounds containing a single quadruple hydrogen bonding unit (4H-unit) per molecule, that are obtained from apolar low molecular weight molecules that have melting points below 45° C. In particular, the present invention relates to supramolecular compounds comprising a low molecular weight, apolar compound, said low molecular weight, apolar compound having a melting point of below 45° C., a molecular weight of about 80 to about 1500 amu and a HLB-value of lower than 8, said low molecular weight, apolar compound bearing a single 4H-unit per molecule.

The invention further relates to a process for the preparation of the supramolecular compounds, wherein the supramolecular compounds are obtainable by
(a) reaction of a 4H-unit with the apolar, low molecular weight compound;
(b) reaction of a precursor of a 4H-unit with an isocyanate functionalised, apolar, low molecular weight compound;
(c) reaction of the apolar, low molecular weight compound with a diisocyanate subsequently followed by a reaction with a precursor of a 4H-unit.

DETAILED DESCRIPTION OF THE INVENTION

In this description and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there is one and only one of the elements. The indefinite article "a" or "an" thus usually means "at least one".

It has unexpectedly been found that modifying apolar low molecular weight compounds with melting points below 45° C. with only one 4H-unit already leads to the formation of supramolecular compounds with polymeric properties like good film-forming, gloss, and ductility, such that they can be used in coating, adhesive and ink compositions. Moreover, these supramolecular compounds have a low melt viscosity when heated above their transition temperature, reflecting their low molecular weight. The low molecular weight compounds that are used to make the supramolecular compounds have melting points below 45° C., are based on apolar (aliphatic) compounds with molecular weights between 80 and 1500 amu that preferably have a molecular weight distribution of less than 1.5, most preferably of about 1, and that contain at least one functional group that is capable of reacting with another functional group. The 4H-unit has preferably an alkyl residue on the 6 position of the isocytosine ring and can be prepared from readily available β-ketoesters. The supramolecular compounds according to this invention have low melt and solution viscosities as they are of low molecular weight and because they only bear one 4H-unit per molecule. Nevertheless, these compounds show polymeric compound properties, thereby displaying unique (supramolecular) behaviour. The compounds of the invention can be prepared with greater ease of synthesis, greater ease of processing at lower processing temperatures, thus benefiting from a significant reduction in time, energy consumption and costs.

The present invention therefore relates to new supramolecular compounds comprising only one 4H-unit, said supramolecular compound being obtainable by reacting: i) an apolar, low molecular weight compound (A) that has a melting point below 45° C., a molecular mass of at least 80 amu, and that contains at least one functional group capable of reacting with another functional group, with iia) a 4H-unit (4H) that contains one or two of such complementary functional groups, or with iib) a linker molecule (L) containing such complementary functional group and another functional group, preferably an isocyanate, followed by the reaction with a precursor of a 4H-unit (4H*). This results in the supramolecular compounds with the general formulas (3), (4), (5), or (6):

A-4H (3)

A-4H-A (4)

A-L-4H* (5)

A-L-4H*-L-A (6)

The molecular weight of the supramolecular compounds according to this invention is 350 to 2000 Dalton, preferably 450 to 1500 Dalton, more preferably 550 to 1200 and most preferably 600 to 900 Dalton.

The supramolecular compounds represented by any of the formulas (3)-(6) will be thermally formed or hardened, in other words, the compounds will be formed by association of a suitable amount of reaction products when lowering the temperature, in particular, by lowering the temperature below a certain transition temperature.

The transition temperature can be defined as the temperature at which a substantial amount of intermolecular physical interactions are formed between the various reaction products (self-assembly). The physical interaction(s), formed between the various molecules, can be reversibly and at least partially broken, in particular by increasing the temperature to a temperature above a certain transition temperature.

The transition temperature can further be defined as the temperature below which the compound shows polymeric compound properties similar to those of thermoplastic compounds at such temperatures such as good film forming and ductile behaviour. In particular, the temperature at which the reaction product shows a tensile modulus of at least 0.05 MPa, preferably at least 0.1 MPa.

Another way to define the transition temperature is the temperature above which one or several intermolecular physical bonds deteriorate. Finally, at a certain temperature above the transition temperature, a liquid is obtained. Generally, the transition temperature lies in the range of about 5° C. to about 100° C. Preferably, the transition temperature lies between about 20° C. and about 90° C., more preferably, between about 30° C. and about 80° C., particularly preferred, between about 40° C. and about 70° C., and most preferred, between about 50° C. and about 60° C.

Description of Compound A

Compound A has preferably a melting point or range below 45° C., preferably below 35° C., and more preferably below 25° C. Compound A has also preferably a melting point higher than −50° C. Compound A has preferably a molecular weight such that the desired polymeric compound properties are obtained in the supramolecular compounds. If the molecular weight of compound A is too low, the resulting supramolecular compound is crystalline and/or too brittle and its solubility in apolar organic solvents is limited. However, if the molecular weight of compound A is too high, the resulting supramolecular compound is too soft and/or tacky. Therefore, the molecular weight of compound A is in between 80 and 1500, more preferably in between 120 and 1000, more preferably between 160 and 800, even more preferably in between 200 and 650, and most preferably in between 220 and 400.

Compound A has at least one functional group available for reaction with the linker molecule L or the 4H-unit (or a precursor 4H* thereof) that is selected from the group consisting of hydroxyl, $C_1$-$C_{20}$ amino, thiol, carboxy, isocyanate, thio-isocyanate, oxyranyl, halogen, azide, and $C_2$-$C_{20}$ ω-alkynyl. Preferably compound A has only one functional group. In another preferred embodiment the functional group is a hydroxyl group or an $C_1$-$C_{20}$ amino group.

Non-limiting examples of compound A are liquids, oils or waxy solids.

Chemically, compound A is an aliphatic compound, an arylated aliphatic compound, a silicone (or polysiloxane) such as particularly a dimethylsiloxane or a phenyl, ethyl or hydro siloxane, a per-fluorinated or partly fluorinated compound, or a combination thereof, where compound A may optionally, but not preferably, contain non-reactive functional groups such as esters, ethers, amides, (thio)urethanes, (thio)ureas or phosphates, preferably esters. Preferably, compound A is aliphatic, arylated aliphatic, is a silicone, or is a combination thereof. More preferably, A is aliphatic or is a silicone, and most preferably, A is aliphatic. The term "aliphatic" includes linear, branched and cyclic structures. The term "aliphatic" also includes that one or more unsaturated bonds may be present in A.

Compound A may only be one compound, and this is preferred, but it may also be a mixture of components or oligomers. In a preferred embodiment of this invention compound A is not a polymer and at least 50 mol % of the mixture that makes up compound A has the same molecular weight, more preferably at least 80 mol %, even more preferably at least 90 mol %, and most preferably at least 95 mol %.

In a preferred embodiment of this invention, A is an apolar, low molecular weight compound or a mixture of apolar, low molecular weight compounds, or A is partly apolar. Preferably, A is an apolar, low molecular weight compound or a mixture of apolar, low molecular weight compounds, most preferably compound A is an apolar compound. Non-limiting examples include liquids, oils, waxy solids, lipids, phospholipids, or sterols. Compound A is preferably non-ionic.

The apolarity of compound A is such that its HLB-value (hydrophile lipophile balance; cf. http://en.wikipedia.org/wiki/Hydrophilic-lipophilic_balance and Ullmann's Encyclopedia of Industrial Chemistry, Emulsions, 2000) is low. If the HLB-number of compound A is not low enough, the resulted supramolecular compound is too hygroscopic and the presence of atmospheric water may negatively influence its polymeric properties. The HLB-value is known in the art and is simply and empirically calculated by determining the molecular weight percentage of the hydrophilic part of a molecule and dividing this percentage by five. Preferably, the HLB value of A is lower than 8, more preferably it is lower than 6, even more preferably it is lower than 4, and most preferably it is lower than 2.

For clarity, and as an explanation of the HLB-value, hydrophobic (or lipophilic) parts of molecules are for example $C_4$-$C_{36}$ linear, branched, or cyclic alkylene, $C_6$-$C_{36}$ arylene or $C_7$-$C_{36}$ alkylarylene groups. Siloxanes or siloxane derivatives, such as dimethylsiloxanes or other silicone groups, and fluorinated groups such as (per)fluoro $C_4$-$C_{36}$ alkylene, $C_6$-$C_{36}$ arylene or $C_7$-$C_{36}$ alkylarylene groups are also hydrophobic. On the other hand, alcohol, amide, ester, urethane, urea and ether groups and compounds (particularly ethylene glycol groups or chains) are considered hydrophilic.

Compound A can be of natural or synthetic origin, preferably compound A is of synthetic origin.

Compound A can be any $C_4$-$C_{36}$ alkyl alcohol, branched, unbranched or cyclic, optionally containing, unsaturated alkene, ether, ester or amide functions. Preferred examples of compound A are linear $C_8$-$C_{24}$, preferably $C_8$-$C_{18}$, aliphatic alcohols such as 1-octanol, 1-decanol, 1-dodecanol, or 1-tetradecanol, branched $C_8$-$C_{24}$, preferably $C_8$-$C_{18}$, alcohols such as 2-hexyl decanol, 2-octyl decanol, 2-octyl tetradecanol, 2-dodecyl hexadecanol (amongst others marketed as Jarcol alcohols by Jarchem Industries, USA), iso-palmitoyl alcohol (Fineoxocol 1600, marketed by Nissan Chemical), iso-stearyl alcohol (Fineoxocol 180, marketed by Nissan Chemical, USA), diols based on dimerized $C_8$-$C_{24}$, preferably $C_8$-$C_{18}$ fatty acids, such as Pripol 2033 (marketed by Uniqema By, the Netherlands), unsaturated $C_4$-$C_{24}$, preferably $C_8$-$C_{24}$, more preferably $C_8$-$C_{18}$ alcohols. Preferred examples of such unsaturated alcohols are citronellol, geraniol, oleyl alcohol, linoleyl alcohol, linolenyl alcohol, or phytol. Compound A can also be selected from the group consisting of steroids or its derivatives such as lanosterol, cholesterol or cholestanol, bile acids or its derivatives, hydrogenated unsaturated alcohols, such as 3,5,7 trimethyl octanol, linear triols such as 1,2,3-trihydroxy-3,7,11,15-tetramethylhexadecane, natural waxes, synthetic waxes, sugar-based fatty alcohols, or any combination of these alcohols. However, according to the present invention, it is preferred that compound A is not cholesterol or a derivative thereof.

Compound A can be any $C_4$-$C_{50}$ hydroxyl functional ester, branched and not branched, optionally containing ester, ether or amide functions. Examples of compound A are castor oil, hydrogenated castor oil, malate esters of $C_4$-$C_{24}$, preferably $C_8$-$C_{24}$, more preferably $C_8$-$C_{18}$ aliphatic alcohols, such as diisostearyl malate or diisostearyl polyglyceryl-3 dimer dilinoleate (both marketed under the Schercemol brand by Lubrizol USA), octyl-ester of hydroxyl-stearate, lactate esters of aliphatic alcohols, or any combination of these esters.

Compound A can be any $C_2$-$C_{36}$ hydroxyl functional mono- or polyester obtained by esterification of a polyol with a $C_4$-$C_{24}$, preferably $C_8$-$C_{24}$, more preferably $C_8$-$C_{18}$ carboxylic ester that is optionally substituted or $C_2$-$C_{36}$ hydroxyl-functional carboxylic acids. Polyols that are suitable for this esterification have preferably 2-60H groups. Preferred examples are glycerol, neopentylglycol, trimethylolpropane, polyglycerol, erithrytol, dipentaerytritol, pentaerithrytol, ditrimethylolpropane, saccharose, glucose, methyl-glucose, sorbitol, fructose, xylose, glucosamine, mannitol, diols based on dimerized $C_8$-$C_{24}$, preferably $C_8$-$C_{18}$ fatty acids, and their mixtures. Carboxylic esters that are suitable for this esterification are for example $C_5$-$C_{60}$ mono-carboxylic acids, $C_3$-$C_{12}$ dicarboxylic acids, branched or unbranched, saturated or unsaturated, specific examples of these are ethyl-hexanoic acid, hexyl-decanoic acid, octyl-dodecanoic acid, palmitoic acid, oleic acid, staeric acid, iso-stearic acid, nonanoic acid, iso-nonanoic acid, arachidonic acid, oxalic acid, adipic acid, succinic acid, fumaric acid, maleic acid, capric acid, decanoic acid, and their mixtures. Hydroxy-functional carboxylic acids that are suitable for this estrerification are for example mono- or poly-hydroxy functional $C_2$-$C_{36}$ carboxylic acids, specific examples are 12-hydroxy stearic acid, ricinoleic acid, malic acid, lactic acid, citric acid and their mixtures.

Compound A can be any hydroxyl-functional silicone, optionally containing amino, ester or amide functions. Examples of compound A are hydroxyethyloxypropyl functional polydimethylsiloxanes, polethyleneoxy functional polydimethylsiloxanes, or amino-functional dimethylsiloxanes. Its is preferred that these polysiloxanes have a molecular weight of 400 to 5500.

Compound A can be any alkyl primary amine or dialkyl secondary amine, where the alkyl groups may be branched, unbranched or cyclic, optionally containing, unsaturated alkene, ether or amide functions. Suitable examples are primary $C_8$-$C_{36}$ aliphatic amines and secondary $C_8$-$C_{36}$ dialkyl amines. Secondary $C_8$-$C_{36}$ dialkyl amines are preferred.

Compound A can be any amine functional silicone or silicone wax, optionally bearing other functional groups such as ethers or amides. Examples are (side chain) amine functional polydimethylsiloxanes, or amine functional silicone waxes (e.g. traded by Genesee Polymer Corporation).

Compound A can be any alkyl carboxylic acid, acid halide or ester, branched, unbranched or cyclic, optionally containing, unsaturated alkene, ether, ester or amide functions. Suitable examples are linear, branched or unsaturated $C_8$-$C_{36}$ alkyl acids, acid halides or esters, for example traded by Jarchem under the names of Jaric (acids) or Jarester (esters).

Compound A can be any $C_8$-$C_{36}$ fluorinated linear, branched or cyclic alkyl, aryl or alkylaryl alcohol, amine or carboxylic acid, where A optionally may contain ether, ester or amide functional groups, or may contain unsaturated groups. Compound A can be partly fluorinated or perfluorinated, and is preferably partly fluorinated. It is also preferred that A is an alcohol or a carboxylic acid, and most preferably A is an alcohol. Suitable examples of these compounds A are 2-(perfluoropropoxy)-2,3,3,3-tetrafluoropropanol, 3-(perfluoro-n-decyl)-prop-2-enol, perfluorododecanoic acid, 1H,1H-perfluoro-1-dodecano 1 or 1H,1H,2H,2H-perfluoro-1-dodecanol.

Preferably, compound A is a $C_2$-$C_{36}$ hydroxyl-functional mono-ester or a $C_4$-$C_{36}$ alkyl alcohol, more preferably, A is an alkyl alcohol, preferably a $C_{12}$-$C_{36}$ alkyl alcohol, and most preferably a branched $C_{14}$-$C_{24}$ alkyl alcohol.

Description of the 4H Unit and Precursor of the 4H-Unit

In general, the structural element that forms the 4H-unit is capable of forming at least four hydrogen bridges (4H) and has the general form (1') or (2') as is disclosed in U.S. Pat. No. 6,320,018, incorporated by reference herein:

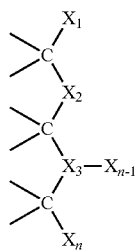

(1')

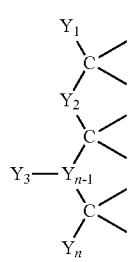

(2')

If the structural element (4H) is capable of forming four hydrogen bridges which is preferred according to the invention, the structural element (4H) has preferably the general form (1) or (2):

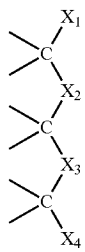

(1)

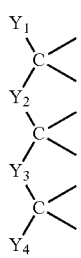

(2)

In all general forms shown above the C—$X_i$ and C—$Y_i$ linkages each represent a single or double bond, n is 4 or more and $X_1 \ldots X_n$, represent donors or acceptors that form hydrogen bridges with the H-bridge-forming unit containing a corresponding structural element (2) linked to them, with $X_i$ representing a donor and Y, an acceptor or vice versa. Properties of the structural element having general forms (1'), (2'), (1) or (2) are disclosed in U.S. Pat. No. 6,320,018 which is expressly incorporated herein by reference.

The structural elements (4H) or 4H-units have at least four donors or acceptors, preferably four donors or acceptors, so that they can in pairs form at least four hydrogen bridges with one another. Preferably the structural elements (4H) have at least two successive donors, followed by at least two acceptors, preferably two successive donors followed by two successive acceptors, preferably structural elements according to general form (1') or more preferably (1) with n=4, in which $X_1$ and $X_2$ both represent a donor and an acceptor, respectively, and $X_3$ and $X_4$ both an acceptor and a donor, respectively. According to the invention, the donors and acceptors are preferably O, S, and N atoms.

Molecules that can be used to construct the structural element (4H) or 4H-units are precursors of the 4H-unit (4H*) and are chosen from nitrogen containing compounds that are reacted with isocyanates, thioisocyanates or activated amines, or that are activated and reacted with primary amines, to obtain a urea or thiourea moiety that is part of the quadruple hydrogen bonding site as is well known in the art. The nitrogen containing compound (4H*) is usually an isocytosine derivative (i.e. a 2-amino-4-hydroxy-pyrimidine derivative) or a triazine derivative, or a tautomer, enantiomer or diastereomer of these derivatives. The isocytosine or triazine derivatives are preferably represented by formulas (7) or (8), as described below. More preferably, the nitrogen containing compound (4H*) is an isocytosine derivative, according to formula (7).

(7)

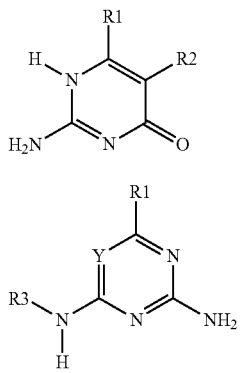

(8)

In the formulas (7) and (8), $R_1$ is selected from the group consisting of hydrogen, phenyl, cyclic, linear or branched $C_1$-$C_{20}$ alkyl groups, wherein the alkyl groups optionally comprise 1-5 heteroatoms selected from the group consisting of oxygen, nitrogen and sulphur, preferably nitrogen or sulphur.

$R_2$ is selected from the group consisting of hydrogen, cyclic, linear or branched $C_1$-$C_{20}$ alkyl groups, wherein the alkyl groups optionally comprise 1-5 heteroatoms selected from the group consisting of oxygen, nitrogen and sulphur.

In structure (8), Y is N or C—$R_4$, preferably Y is N.

In structure (8), $R_3$ and $R_4$ are independently selected from the group consisting of hydrogen, cyclic, linear or branched $C_1$-$C_{20}$ alkyl groups or $C_6$-$C_{20}$ arylalkyl or alkylaryl groups, wherein the alkyl groups optionally comprise 1-5 heteroatoms selected from the group consisting of oxygen, nitrogen and sulphur, preferably nitrogen or sulphur. Preferably, $R_3$ and $R_4$ are independently selected from the group consisting of hydrogen, methyl, ethyl, isopropyl or phenyl. Most preferably, $R_3$ and $R_4$ are both a hydrogen.

In structure (7), $R_1$ and $R_2$ are preferably not connected to form a fused cyclic structure, as such fused structures generally lead to less-processable building blocks. Likewise, in structure (8), $R_3$ and $R_4$ are preferably not connected to form a fused ring structure.

Preferably, $R_1$ is a cyclic, linear or branched $C_1$-$C_6$ alkyl group or a phenyl, more preferably $R_1$ is a linear or branched $C_1$-$C_4$ alkyl group, most preferably a methyl.

Preferably, $R_2$ is hydrogen or a linear or branched $C_1$-$C_6$ alkyl group optionally comprising 1-2 heteroatoms from the group consisting of oxygen and nitrogen, more preferably hydrogen or a linear or branched $C_1$-$C_4$ alkyl group comprising 1-2 oxygen atoms, even more preferably hydrogen or β-hydroxy-ethyl, most preferably β-hydroxy-ethyl.

Preferred 4H-units are depicted in formulas (9) and (10)

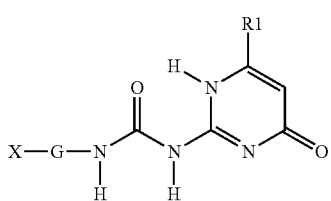

(9)

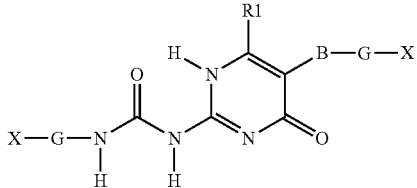

(10)

In the formulas (9) and (10), $R_1$ is defined as above;

G is a linking moiety that is selected from the group consisting of cyclic, linear or branched $C_1$-$C_{20}$ alkylene or $C_6$-$C_{20}$ arylene groups, wherein the alkylene and arylene groups optionally comprise 1-5 heteroatoms selected from the group consisting of oxygen, nitrogen and sulphur, and wherein the arylene groups are optionally substituted with one or more linear, cyclic or branched $C_1$-$C_{20}$ alkyl and/or alkylene groups;

B is a linking moiety selected from the group consisting of cyclic, linear or branched $C_1$-$C_{20}$ alkylene or $C_6$-$C_{20}$ arylene groups, wherein the alkylene and arylene groups optionally comprise 1-5 heteroatoms selected from the group consisting of oxygen, nitrogen and sulphur, wherein the arylene groups are optionally substituted with one or more cyclic, linear or branched $C_1$-$C_{20}$ alkyl and/or alkylene groups, and wherein B optionally comprises a functional group such as a (thio)urethane, ester, amide or (thio)urea;

X is a reactive functional group independently selected from the group consisting of —NCO, —NCS, —OH, —SH, —NHC(Z)Q, —NHR$_5$, oxiranyl, —C(Z)ZR$_6$ and —C(Z)NHR$_6$ wherein R$_5$ and R$_6$ are independently selected from the group consisting of hydrogen, linear, cyclic or branched $C_1$-$C_6$ alkyl, $C_6$-$C_{20}$ aryl groups, $C_7$-$C_{20}$ alkaryl groups and $C_7$-$C_{20}$ arylalkyl groups, wherein Q is a leaving group such as a imidazole group, a succidimyl group, a caprolactam group or a (substituted) phenol group, and wherein Z is independently O or S.

Preferably, G is selected from linear, cyclic or branched $C_2$-$C_{13}$ alkylene or a $C_6$-$C_{13}$ arylene group, wherein the arylene group is optionally substituted with linear or branched $C_1$-$C_6$ alkyl or alkylene groups. More preferably, G is a branched $C_9$-$C_{13}$ alkylene or $C_6$-$C_{13}$ arylene group, wherein the arylene group is optionally substituted with linear or branched $C_1$-$C_6$ alkyl or alkylene groups. Most preferably, G is a 3-methylyl-3-methyl-5,5-dimethyl cyclohexyl group (i.e. an isophoronyl linking group).

Preferably, B is a linear or branched $C_1$-$C_6$ alkylene group, wherein B optionally comprises an amide, urea, ester or urethane functional group that connects this $C_1$-$C_6$ alkylene group with the linking moiety G. More preferably, B is a linear or branched $C_1$-$C_6$ alkylene groups, wherein B optionally comprises a urethane functional group. Most preferably, B is an ethylene urethane linking moiety (i.e. CH$_2$CH$_2$OC(O)NH).

X is preferably —NCO, —NCS, —SH, oxiranyl or —NHR$_5$. More preferably, X is —NCO or —NHR$_5$, wherein R$_5$ is a hydrogen atom or a linear or branched $C_1$-$C_6$ alkyl group, more preferably a hydrogen atom. Most preferably, X is —NCO.

Description of the Linker Molecule L

The linker molecule L is a bifunctional molecule, preferably a diisocyanate, a dithioisocyanate, a bifunctional molecule having two activated primary amine groups or a diamine with two primary amine groups. Therefore, these bifunctional linker molecules L preferably have the schematic form:

X-G-X wherein G is defined as above and wherein X is chosen from —NCO, —NCS, —NHC(O)Q, —NHC(S)Q or —NH$_2$, wherein Q is a leaving group, preferably an imidazole group, a succidimyl group, a caprolactam group or a (substituted) phenol group. Preferably, X is —NCO or —NCS, more preferably —NCO. In this embodiment, X-G-X is more preferably, an alkylene diisocyanate wherein the alkylene group comprises 1-20 carbon atoms and wherein the alkylene group may be linear, cyclic or branched, preferably linear, or an arylene diisocyanate, wherein the arylene group comprises 6-20 carbon atoms and may be substituted with alkyl or alkylene groups comprising 1-6 carbon atoms. The bifunctional molecule is even more preferably 2,2,4-trimethyl-hexane diisocyanate, 2,4,4-trimethyl-hexane diisocyanate, isophoronediisocyanate, ethyl or methyl lysine diisocyanate, 4,4'-methylenebis(cyclohexyl isocyanate), or 4,4'-methylene bis(phenyl isocyanate), more preferably 2,2,4-trimethyl-hexane diisocyanate, 2,4,4-trimethyl-hexane diisocyanate or isophoronediisocyanate, and most preferably isophorone diisocyanate.

Less preferred linker molecules L are bifunctional molecules with two different reactive groups X, where one of these reactive groups X is a primary amine, an activated primary amine, an isocyanate or a thio-isocyanate. The linking moiety G is then also defined as above. In this less preferred embodiment, one of both reactive groups X is most preferably a primary amine group.

Description and Synthesis of the Supramolecular Compound

According to the invention, the supramolecular compounds are preferably prepared by the following methods: reaction between i) an apolar low molecular weight molecule that has a melting point below 45° C., a molecular mass of at least 80 amu, and that contains at least one functional group that is capable of reacting with another functional group, with (ii)(a) a 4H-unit with one or two complementary functional groups or (ii)(b) a linker molecule (L) containing a functional group and an isocyanate function, followed by reaction with a precursor of a 4H-unit.

According to a first method, compound A is reacted in a first step with the linker compound that has at least two functional groups (L). In a subsequent step, the product obtained in the first step is reacted with the precursor of the 4H-unit (4H*). Suitable and preferred structures of A, L and 4H* are described above. These reactions can be performed with or without solvents. Preferably, the reaction in the first step is performed without added solvent at temperatures below 60° C., more preferably below 40° C., and even more preferably below 25° C. The precursor of the 4H-unit can be present already at the first reaction step, or can be added after the first reaction step has been completed, i.e. all the molecules A have reacted with L. All of the apolar compounds A or linker molecules L may be added directly at the beginning of the reaction, or they may (independently) be slowly added during the first reaction step. The second step is preferably performed between 80° C. and 180° C., more preferably between 100° C. and 145° C., more preferably between 110° C. and 140° C., and most preferably between 115° C. and 135° C. The second step may be performed without the addition of solvent, but preferably is performed in the presence of a high boiling polar non-protic solvent such as dimethylsulfoxide, N-methylpyrolidone, dimethylformamide, dimethylacetamide, propylenecarbonate, ethylene carbonate, dimethoxyethane, butylacetate, ethyleneglycol diacetate, propyleneglycol diacetate, ethyleneglycol-methylether acetate, pyridine(s), 1-N-methyl imidazole, dioxane, methyltetrahydrofuran or methylisobutyl ketone. The amount of solvent present during this second reaction step is in between 0 and 80% by weight, more preferable in between 1 and 50% by weight, even more preferable in between 5 and 40% by weight, most preferably in between 10 and 30% by weight. In a preferred embodiment of this invention, the preparation takes place according to a one-pot procedure in which all the reactants A, L, and 4H* are present in the desired ratio at the first reactions step, optionally after slow addition of A and/or L, and the second reaction step is initiated after completion of the first reaction step by raising the temperature to a temperature in between 80° C. and 180° C. and/or the addition of a polar non-protic solvent.

According to a second method, compound A is reacted with the 4H-unit that contains a reactive functional group capable of reacting with A. Suitable and preferred structures of A and 4H-unit are described above. This reaction can be performed with or without solvents. Preferably, the reaction is performed between 20° C. and 180° C., more preferably between 40° C. and 145° C., more preferably between 60° C. and 140° C., and most preferably between 60° C. and 125° C. The second step may be performed without the addition of solvent, but preferably is performed in the presence of a non-protic solvent such as dimethylsulfoxide, N-methylpyrollidone, dimethylformamide, dimethylacetamide, propylenecarbonate, ethylenecarbonate, dimethoxyethane, butylacetate, ethylacetate, ethyleneglycol diacetate, propyleneglycol diacetate, ethyleneglycol-methylether acetate, methyl-ethyl keton, t-butyl-methyl keton, methylisobutyl ketone, toluene, xylene, tetrahydrofuran, methyl-tetrahydrofuran, dioxane, alkanes or chloroform. The amount of solvent present during this second reaction step is in between 0 and 80% by weight, more preferable in between 5 and 60% by weight, even more preferable in between 10 and 50% by weight, most preferably in between 10 and 30% by weight.

According to these methods, L is preferably a diisocyanate and the 4H-unit contains preferably an isocyanate group as a reactive functional group. In another preferred embodiment of this invention 4H* and the 4H-unit contain two functional groups such that structures (4) or (6) are obtained.

Preferably, the molar ratio is preferably chosen as such that only one compound A reacts with one complementary reactive functional group of the 4H-unit or one reactive functional group of the linker molecule L. In a preferred embodiment of the invention, the molar ratio between compound A and the complementary functional group of the 4H-unit, or the functional group of the linker molecule, is about 0.8:2.0, more preferably 0.8:1.2, and most preferably about 1:1.

The preparation of the supramolecular compounds presented in this invention can be done by any method known in the art, for example by stirring in a reaction vessel, by mixing in a cup, by using a Banbury-type mixer, by using a Brabender mixer, by using a single screw extruder, or by using a twin screw extruder.

In one embodiment of the invention no catalyst is added to the reaction mixture, for example, when isocyanates are reacted with amines or in some cases where no stoichiometric amounts of reactants are used. This is preferred when complete absence of residual catalyst is required for the use of the compound. In another embodiment of this invention, a catalyst is added to the reaction mixture that promotes the reactions between the complementary groups. Examples are catalysts known in the art that promote the reaction between isocyanates and hydroxyl groups that are derived from tertiary amines such as 1,4-diazabicyclo[2.2.2]octane (DABCO) or 1,8-diazabicyclo[5.4.0]undec-7-ene (DBU), or derived from transition metals, such as tin(II) octanoate, dibutyltin(IV) laurate or zirconium acetoacetate. Preferably, these catalyst are tin(II) or tin(IV) compounds. The amount of catalyst is generally below 1% by weight, preferably below 0.5% by weight and most preferably below 0.2% by weight of the total amount of reactants.

In one preparation more than one type of molecule A, L, 4H* or 4H-unit may be present such that a mix of different molecules is obtained that all constitute the supramolecular compound. In addition, also other molecules may be present in the preparation. For example molecules that have been formed by the reaction of two molecules A with one molecule L, represented by formula (II):

A-L-A (11)

Additionally, active ingredients may be added to the preparation such as dyes, pigments, rheology modifiers, compatibilizers, UV-stabilizers, anti-oxidants, flame-retardants or flow agents. Also inorganic fillers may be present such as ceramics, clays, titanium dioxide, fumed silica, calcium oxide, calcium carbonate, hydroxy apetite. Optionally, polymeric molecules with two or more 4H-units may be added.

Applications of the Supramolecular Compound

The supramolecular compounds according to the invention can be applied in various technical areas, examples being coatings, biomedical coatings, inks, toner resins, lacquers, adhesives, and glues. The resulting supramolecular compounds according to the invention form solids that are preferably be used in coating, adhesive or ink compositions, while their melt-viscosity remains low.

The supramolecular compound of the invention can be applied on different substrates such as, for example, glass, paper, wood, plastic, brick, and metals such as aluminum and iron. Biomedically relevant substrates such as for example stainless steel, polyethylenes or polyesters are also of interest. Possible interesting applications can be, for example, in powder coatings, hot melt inks and hot melt adhesives. It can be particularly useful to apply the supramolecular compound according to the present invention in coatings for heat sensitive substrates, sizing of fibers, or adhesive in textile applications.

In the art, coatings generally consist of thermosetting compounds, which are hardened by crosslinking upon being heated or under the effect of ultraviolet radiation (UV-curable compositions). Said UV-curable compositions generally comprise an oligomer system, reactive diluent(s), expensive photoinitiator compounds, and other additives. For applying such UV-curable coating compositions, the resin is applied on the substrate in the non-crosslinked state (the still-liquid state), and then to run through an apparatus suitable for supplying thereto the energy which is required for causing crosslinking to take place. Such apparatus must include ultraviolet lamps associated with matching reflectors for focussing the radiation on the substrate. Such apparatus is complex, requires continuous maintenance and is thus relatively expensive.

The supramolecular compound or mixture of supramolecular compounds according to the present invention can be used as a coating to which a colouring agent, such as a pigment or dye has been added. In practice, the supramolecular compound or mixture of supramolecular compounds of the invention, optionally in the presence of one or more solvents, can be applied as a liquid to the substrate at a temperature above the transition temperature and can subsequently be hardened by cooling to a temperature below the transition temperature. The transition temperature being defined as above. The cooling can, for example, be performed by means of a conventional cooling system, or by leaving the treated substrate at ambient temperature, or by causing it to run through a bath of water or another cooling liquid or gas.

The coating, ink or matrix comprising the supramolecular compound or mixture of supramolecular compounds according to the present invention should not delaminate (and preferably show polymeric mechanical properties) at the temperatures of use. The temperatures of use can be defined as those temperatures at which the cured coating or ink is used. The temperatures of use preferably range from about −100° C. to about 100° C., more preferably from about −50° C. to about 80° C., particularly preferred from about −40° C. to about 70° C., most preferred from about −25° C. to about 50° C. In particular at room temperature the coating is in the hardened state.

When the compound of this invention is used in biomedical coatings, it is preferred that compound A is related to or derived from a natural lipid or a phospholipid. Examples are (phospho)lipids derived from glycerol, such as for example 1,2-distearoyl glycerol or 1,2-distearoyl-sn-glycero-3-phosphoethanolamine. In this application field it may also be of interest that the linker molecule L is derived from or related to a natural compound. Examples are butyl diisocyanate or diisocyanates derived from lysine. Finally, when used as a biomedical compound, specific (bioactive) additives used in the biomedical arena may be added to the compound of this invention, such as peptides, proteins, anti-oxidants, lubricants, etc. Peptides with 4H-units may also be added to the compound of this invention.

The person skilled in the art of coatings can control the composition of the supramolecular compound or mixture of supramolecular compounds according to the present invention depending on the properties he is looking for and wanting to achieve. For instance, by changing the molecular weight and/or the branching of compound A, soft or hard portions can be introduced depending on which type of coating is required.

EXAMPLES

The following examples further illustrate the preferred embodiments of the invention. When not specifically mentioned, chemicals are obtained from Aldrich.

Example 1

Bifunctional Precursor of 4H-Unit

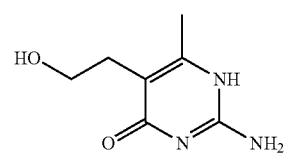

2-Acetylbutyrolactone (2 mL) and guanidine carbonate (3.3 g) were put to reflux in absolute ethanol (20 mL) in the presence of triethylamine (5.2 mL). The solution became yellow and turbid. After overnight heating at reflux, the solid was filtered, washed with ethanol, and suspended in water. The pH was adjusted to a value of 6-7 with an HCl-solution, and the mixture was stirred for a while. Filtration, rinsing of the residue with water and ethanol and subsequent drying of the solid gave the pure product. $^1$H NMR (400 MHz, DMSOd$_6$): δ 11.2 (1H), 6.6 (2H), 4.5 (1H), 3.4 (2H), 2.5 (2H), 2.1 (3H). FT-IR (neat): ν (cm$^{-1}$) 3333, 3073, 2871, 1639, 1609, 1541, 1487, 1393, 1233, 1051, 915, 853, 789, 716.

Example 2

Monofunctional 4H-Unit

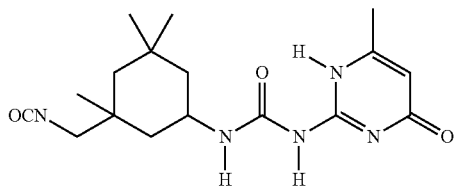

2-Amino-4-hydroxy-6-methylpyrimidine (5.2 g) was added to isophoronediisocyanate (IPDI, 50 mL) and subsequently stirred at 90° C. under an argon atmosphere for 3 days. The resulting clear solution was precipitated in heptane. The white gum was collected, heated in 150 mL heptane, cooled on ice, and filtered. The same procedure was repeated once more with the white residue, resulting in a white powder. $^1$H NMR (400 MHz, CDCl$_3$): δ 13.1 (1H), 12.0 (1H), 10.1 (1H), 5.9 (1H), 4.1-3.1 (3H), 2.1 (3H), 2.0-0.9 (15H). FT-IR (neat): ν (cm$^{-1}$) 2954, 2255, 1696, 1662, 1582, 1524, 1247. This compound is obtained as 4 different regio-isomers, only one of the four possible structures is depicted.

Example 3

Bifunctional 4H-Unit

2-Amino-4-hydroxy-5-(2-hydroxy ethyl)-6-methyl-pyrimidine (12 gram, obtained in Example 1) was suspended in IPDI (150 mL) and was stirred for a few days at 90° C. under an argon atmosphere. A clear solution developed. The solution was cooled and precipitated in hexane. The solid was filtered, stirred in another portion of hexane, and then the product was isolated by filtration, washing with hexane and drying of the residue, resulting in a white glass. Yield: 98%. $^1$H NMR (400 MHz, CDCl$_3$): δ 13.1 (1H), 11.9 (1H), 10.2 (1H), 4.8-4.5 (1H), 4.2 (2H), 4.0-3.2 (3H), 3.1-2.9 (3H), 2.7 (2H), 2.3 (3H), 1.9-1.6 (4H), 1.4-0.8 (26H). FT-IR (neat): ν (cm$^{-1}$) 2954, 2254, 1690, 1664, 1637, 1590, 1532, 1461, 1364, 1307, 1257, 1034, 791. MALDI-TOF-MS, [M$^+$]=614, [M+Na$^+$]=636. This compound is obtained as 8 different regio-isomers, only one of the eight possible structures is depicted.

Example 4

2-Decyl-tetradecanol (HLB-value=1.0; melting point=17-20° C.) with a monofunctional 4H-unit To a solution of 2-decyl-1-tetradecanol (19.62 g) in chloroform (50 mL) was added the compound of Example 2 (23.1 g) and 3 drops of DBTDL (dibutyl tin dilaurate). The reaction mixture was subsequently stirred at 65° C. in an argon atmosphere for 16 h. Hereafter, the solvent was removed by evaporation using a rotary evaporator. The resulting compound was redissolved in pentane (100 mL) and filtered over celite followed by removal of the solvent in vacuo, resulting in a slight yellowish glass. $^1$H NMR (400 MHz, CDCl$_3$): δ 13.1 (1H), 11.9 (1H), 10.2 (1H), 5.8 (1H), 4.8-4.3 (1H), 4.2-3.6 (3H), 3.1-2.9 (2H), 2.2 (3H), 1.9-0.6 (62H).

Example 5

2-Hexyl-decanol (HLB-value=1.4; melting point=−21-−15° C.) with a monofunctional 4H-unit 2-Hexyl-1-decanol (51.3 g) was dried in vacuo at 60° C. for 1 hour. This dried alcohol was subsequently slowly added to a stirred mixture of IPDI (47.1 g) and DBTDL (22 mg) at 50° C. over a period of 5 hours. After all the alcohol had been added, the mixture was stirred for one additional hour followed by the addition of 6-methylisocytosine (31.8 g) and propylenecarbonate (40 mL, water free), The reaction mixture was heated to 140° C. and stirred for almost 2 hours under an argon atmosphere. Hereafter, the reaction mixture was cooled down and diluted with heptane (200 mL) followed by filtration over celite. The filtrate was washed with methanol, followed by removal of the solvent in vacuo, resulting in a

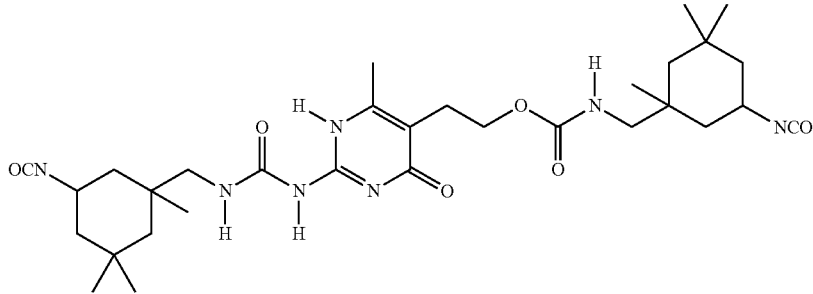

clear glass. $^1$H NMR (400 MHz, CDCl$_3$): δ 13.1 (1H), 11.9 (1H), 10.2 (1H), 5.8 (1H), 4.8-4.3 (1H), 4.2-3.6 (3H), 3.1-2.9 (2H), 2.2 (3H), 1.9-0.6 (46H).

Example 6

2-Hexyl-decanol (HLB-value=1.4; melting point=−21-−15° C.) with a bifunctional 4H-unit 2-Hexyl-1-decanol (31.3 g) was dried at 70° C. in vacuo and was thereafter dissolved in dry chloroform (200 mL). The 4H-unit compound of Example 3 (47.5 g) and 6 drops of DBTDL were added and the reaction mixture was subsequently stirred at 65° C. in an argon atmosphere for 16 h. The mixture was concentrated to about 150 mL and was stirred at 65° C. for another night. Thereafter, the solvent was removed by evaporation using a rotary evaporator. The resulting compound was redissolved in pentane (150 mL) and filtered over celite followed by removal of the solvent in vacuo, resulting in a slightly yellowish glass. $^1$H NMR (400 MHz, CDCl$_3$): δ 12.9 (1H), 11.9 (1H), 10.1 (1H), 5.1-4.3 (2H), 4.2-3.6 (8H), 3.2-2.5 (6H), 2.2 (3H), 1.9-0.6 (92H).

Example 7

Diisostearyl Malate (HLB-Value=3.6; Melting Point<−5° C.) Functionalized with a Bifunctional 4H-Unit Diisostearyl malate, or hydroxy diisostearyl malate (9.8 g, obtained from Lubrizol Corporation, USA), was dried in vacuo at 80° C. for 1 hours. After cooling down of the dried alcohol to 50° C., IPDI (3.22 g) and DBTDL (4 mg) were added and the reaction mixture was stirred overnight at 60° C. under an argon atmosphere. Subsequently, propylenecarbonate (5.5 mL, water free) and the isocytosine of Example 1 (1.36 g) were added and the reaction mixture was heated to 120° C. and stirred for 3 hours under an argon atmosphere. Hereafter, the reaction mixture was cooled down and diluted with heptane (50 mL) followed by filtration over celite. The filtrate was washed with methanol, followed by removal of the solvent in vacuo, resulting in a clear glass. $^1$H NMR (400 MHz, CDCl$_3$): δ 13.2-12.8, 12.0-11.7, 10.3-9.6, 5.4, 5.0-4.3, 4.2-3.6, 3.2-2.5, 2.2, 2.0-0.5.

Alternatively, this reaction has also been executed by having the isocytosine of Example 1 already present in the reaction mixture from the beginning Accordingly, the diisostearyl malate alcohol and the isocytosine from Example 1 are mixed and dried, IPDI is added and reacted with the alcohol at 50° C. for 3 hours under the influence of the also added DBTDL, dry propylene carbonate is added and the mixture is then heated to 130° C. for 3 hours to form the product. Ratios of reactants and solvents, work-up and result are similar as described above.

Example 8

Diisostearyl Malate (HLB-Value=3.6; Melting Point<−5° C.) Functionalized with a Monofunctional 4H-Unit by an Alternative Reaction Route In the first step, the diisostearyl malate (compound A) is activated with carbonyl diimidazole (CDI). Next, this activated compound is reacted with isophorylamine modified 4H-unit. This molecule has been prepared by reacting an excess of isophoryl diamine (linker molecule L) with CDI-activated methyl isocytosine (precursor of the 4H-unit).

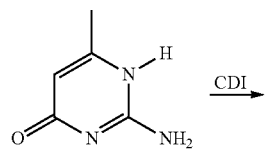

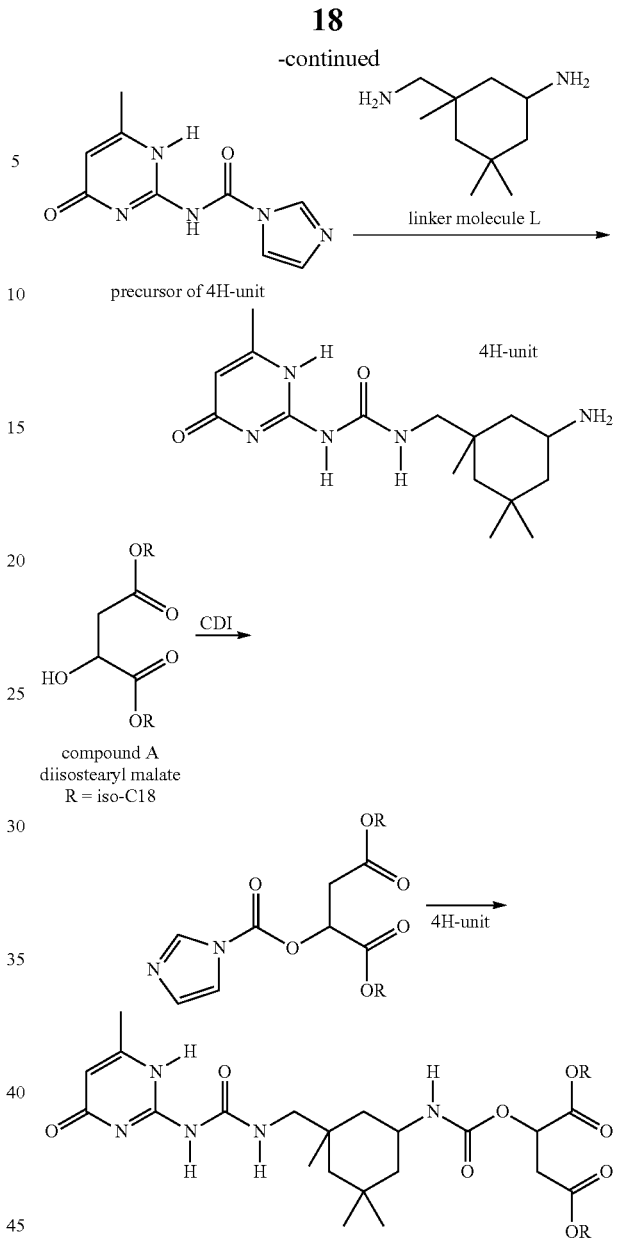

This alternative approach, see the scheme above, exemplifies that the compounds of this invention can also be prepared by using other reactive functional groups X than isocyanates or thioisocyanates, enabling the use of a further variety of linking moieties G.

Comparative Example A

Compound A+Linker L Only

2-Hexyl-1-decanol (7.58 g; HLB-value=1.4; melting point=−21−−15° C.) was dried in vacuo at 60° C. for 2 hours. This dried alcohol was subsequently slowly added to a stirred mixture of IPDI (6.90 g) and DBTDL (11 mg) at 50° C. over a period of 5 hours. After all the alcohol had been added, the mixture was stirred for one additional hour followed by the addition of dibutyl amine (6 mL). The reaction mixture was heated to 100° C. and stirred for 2 hours under an argon atmosphere. Hereafter, the reaction mixture was cooled down and diluted with dichloromethane (30 mL) and extracted with water (2 times). The organic fraction was dried on $Na_2SO_4$, followed by filtration and removal of the solvent in vacuo, resulting in a clear tacky oil. $^1$H NMR (400 MHz, $CDCl_3$): δ 4.8-4.3 (2H), 4.2-3.6 (3H), 3.2-2.9 (6H), 1.8-0.8 (60H).

Comparative Example B

Supramolecular Compound with Two 4H Units

Pripol 2033 (25.7 g, α,ω-bis-hydroxyfunctional C36 compound (HLB-value=1-2; liquid at 20° C.) obtained from Uniqema BV) was dried at 80° C. in vacuo for 2 hours followed by cooling down to 20° C., dilution with xylene (15 mL) and addition of IPDI (19.9 g) and 4 drops of DBTDL. This mixture was stirred under an argon atmosphere at 20° C. for 12 h. Subsequently, 2-amino-4-hydroxy-6-methylpyrimidine (11.5 g) was added, and the reaction mixture was diluted with propylene carbonate (10 mL) and heated to 140° C. After 4 hours stirring at 140° C. the reaction mixture was cooled to room temperature, diluted with THF (250 mL), filtrated over celite, and precipitated in cold methanol. The precipitate was collected, washed with methanol, and dried in vacuo resulting in a slight yellow glass. $^1$H NMR (400 MHz, $CDCl_3$): δ 13.1 (2H), 11.9 (2H), 10.2 (2H), 5.8 (2H), 4.8-4.3 (2H), 4.2-3.6 (6H), 3.1-2.9 (4H), 2.2 (6H), 1.9-0.6 (ca. 96H).

Comparative Example C

Compound A Directly Linked to 4H Unit

The compound of example 2 (1.23 g) was dissolved in butanol (6 mL) together with 1 drop of DBTDL and subsequently stirred for 1 hour at 80° C. Hereafter, the reaction mixture was dried in vacuo, resulting in a white brittle solid. $^1$H NMR (400 MHz, $CDCl_3$): δ 13.1 (1H), 11.9 (1H), 9.9 (1H), 5.8 (1H), 5.0-4.4 (1H), 4.2-3.6 (3H), 3.1-2.9 (2H), 2.2 (3H), 1.9-0.6 (22H).

Example 9

Melt Viscosity Data

Table 1: Melt viscosities of Example 5, Comparative Example A, and Comparative Example B. Viscosities measured with a Haake VT500 with FL1000 spindle, temperature controlled with a thermostatted oil bath (Table 1).

As can be seen from Table 1, Example 5 according to this invention shows a strong temperature dependency in its melt viscosity: a liquid like viscosity at 140° C. and very high melt viscosity at 40° C. In contrast, comparable example B which comprises two 4H-units per molecule and which has a comparable molecular weight per 4H-unit as Example 5, has a melt viscosity which is almost 350 times higher than Example 5. Clearly, the presence of just one 4H-unit per molecule results in a much lower melt viscosity. In contrast, Comparative example A in which the precursor of the 4H-unit is replaced by dibutylamine (there is no 4H-unit in the molecular structure) has a low melt viscosity over the complete temperature range, where at 40° C. Comparative Example A is a liquid. This shows that the 4H-unit is needed in the molecule to obtain polymeric properties.

TABLE 1

| Temperature | Example 5 | Comparative example A | Comparative example B |
|---|---|---|---|
| 140° C. | 2.1 Pa · s | a | 780 Pa · s |
| 120° C. | 17 Pa · s | a | 9500 Pa · s |
| 100° C. | 106 Pa · s | a | 90 kPa · s |
| 80° C. | 1150 Pa · s | a | b |
| 60° C. | 24 kPa · s | 1.4 Pa · s | b |
| 40° C. | 700 kPa · s | 7.5 Pa · s | b | a: too low to be measured in this set-up
b: too high to be measured in this set-up Example 10

Thermally Applied Coating on a Flexible Substrate

A PET-film was used as a substrate for the coating. This film was covered with powdered compound obtained from Example 7. Heating the substrate to 130° C. for 5 minutes, followed by cooling to 25° C., resulted in a nice glossy and transparent coating that did not show delamination upon bending of the substrate.

In contrast, applying powdered compound of Comparative Example C in the same way, resulted in the formation of an inhomogeneous coating due to limited flow of the compound at 130° C. Moreover, adhesion of this compound to the substrate was poor as delamination occurred upon bending of the substrate.

Example 11

Hot Melt Adhesive for Glass Substrates

A glass slide was covered with compound obtained in Example 4. After heating the glass slide to 140° C. for 5 minutes, another glass slide was put on top and was held in place upon cooling to 25° C. After cooling down, the two glass slides were adhered firmly to each other and could only be detached by applying a load over 1 kg.

In contrast, applying the compound of Comparative Example A in the same way, did not result in the formation of a constructive bond between the glass slides as they debonded spontaneously (already on their own weight).

The invention claimed is:

1. A process for preparing a supramolecular compound comprising a single 4H-unit per molecule or a single 4H*-unit per molecule, wherein,
   a compound A having a melting point of below 45° C., a molecular weight of about 160 to about 800 amu and a HLB-value of lower than 8, said compound A is a branched, unbranched or cyclic $C_1$-$C_{100}$ alkyl alcohol, compound A optionally being substituted with alkenyl, ether, ester or amide groups, is reacted with:
   a 4H-unit; or
   a linker L having the formula X-G-X, wherein X is independently selected from the group consisting of —NCO, —NCS, —OH, —SH, —NHC(Z)Q, —$NHR_5$, oxiranyl, —C(Z)$ZR_6$ and —C(Z)$NHR_6$, wherein Q is a leaving group, Z is independently O or S, and $R_5$ and $R_6$ are independently selected from the group consisting of hydrogen, linear, cyclic or branched $C_1$-$C_6$ alkyl groups, $C_6$-$C_{20}$ aryl groups, $C_7$-$C_{20}$ alkaryl groups and $C_7$-$C_{20}$ arylalkyl groups;
   and wherein G is a cyclic, linear or branched $C_1$-$C_{20}$ alkylene or a $C_6$-$C_{20}$ arylene group, followed by the reaction with a 4H*-unit;

wherein:

said 4H* has the formula (7) or formula (8):

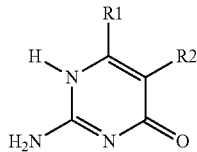
(7)

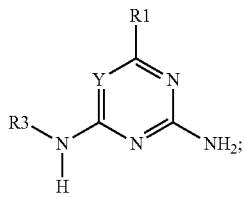
(8)

said 4H-unit having the formula (9) or the formula (10):

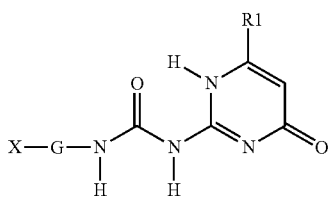
(9)

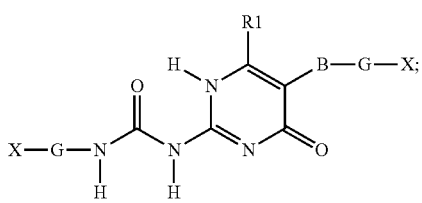
(10)

wherein:

G and X are defined as above;

$R_1$ is selected from the group consisting of hydrogen, phenyl, cyclic, and linear or branched $C_1$-$C_{20}$ alkyl groups, wherein the alkyl groups optionally comprise 1-5 heteroatoms selected from the group consisting of oxygen, nitrogen and sulphur;

$R_2$ is selected from the group consisting of hydrogen, and cyclic, linear or branched $C_1$-$C_{20}$ alkyl groups, wherein the alkyl groups optionally comprise 1-5 heteroatoms selected from the group consisting of oxygen, nitrogen and sulphur;

$R_3$ and $R_4$ are independently selected from the group consisting of hydrogen, cyclic, linear or branched $C_1$-$C_{20}$ alkyl groups and $C_6$-$C_{20}$ arylalkyl or alkylaryl groups, wherein the alkyl groups optionally comprise 1-5 heteroatoms selected from the group consisting of oxygen, nitrogen and sulphur;

B is a linking moiety selected from the group consisting of cyclic, linear or branched $C_1$-$C_{20}$ alkylene and $C_6$-$C_{20}$ arylene groups, wherein the alkylene and arylene groups optionally comprise 1-5 heteroatoms selected from the group consisting of oxygen, nitrogen and sulphur, wherein the arylene groups are optionally substituted with one or more cyclic, linear or branched $C_1$-$C_{20}$ alkyl and/or alkylene groups; and Y is N or C—$R_4$.

2. The process according to claim 1, wherein said compound A is reacted with said 4H unit.

3. The process according to claim 1, wherein said compound A is reacted with said linker L to obtain a product comprising at least one isocyanate group, which is then reacted with the 4H* unit.

4. The process according to claim 1, wherein said compound A is reacted with a diisocyanate to obtain a product, which is then reacted with the 4H* unit.

5. The process according to claim 4, wherein the leaving group comprises an imidazole group, a succidimyl group, a caprolactam group or a substituted phenol group.

6. The process according to claim 1, wherein compound A is selected from the group of $C_4$-$C_{36}$ alkyl alcohols.

7. The process according to claim 1, wherein compound A is selected from the group consisting of linear $C_8$-$C_{24}$ alcohols and branched $C_8$-$C_{24}$ alcohols.

8. The process according to claim 6, wherein compound A is selected from the group consisting of linear $C_8$-$C_{24}$ alcohols and branched $C_8$-$C_{24}$ alcohols.

9. The process according to claim 7, wherein compound A is selected from the group consisting of 2-hexyl decanol, 2-octyl decanol, 2-octyl tetradecanol, 2-dodecyl hexadecanol, and iso-palmitoyl alcohol, and unsaturated alcohols selected from the group consisting of citronellol, geraniol, oleyl alcohol, linoleyl alcohol, linolenyl alcohol, and phytol.

10. The process according to claim 8, wherein compound A is selected from the group consisting of 2-hexyl decanol, 2-octyl decanol, 2-octyl tetradecanol, 2-dodecyl hexadecanol, and iso-palmitoyl alcohol, and unsaturated alcohols selected from the group consisting of citronellol, geraniol, oleyl alcohol, linoleyl alcohol, linolenyl alcohol, and phytol.

11. The process according to claim 1, wherein in formula (7) $R_1$ is methyl and $R_2$ is hydrogen or β-hydroxy ethyl.

* * * * *